(12) United States Patent
Aoi et al.

(10) Patent No.: US 8,101,933 B2
(45) Date of Patent: Jan. 24, 2012

(54) MEDICAL DEVICE

(75) Inventors: Tatsufumi Aoi, Hiroshima (JP); Susumu Urano, Hiroshima (JP); Shuji Kaneko, Hiroshima (JP); Hiroyuki Shibata, Hiroshima (JP); Seinoshin Hamanaka, Minato-ku (JP)

(73) Assignee: Mitsubishi Heavy Industies, Ltd., Tokyo (JP)

( * ) Notice: Subject to any disclaimer, the term of this patent is extended or adjusted under 35 U.S.C. 154(b) by 462 days.

(21) Appl. No.: 11/826,929

(22) Filed: Jul. 19, 2007

(65) Prior Publication Data

US 2008/0197303 A1    Aug. 21, 2008

(30) Foreign Application Priority Data

Feb. 16, 2007    (JP) ................. 2007-036354

(51) Int. Cl.
*H01J 29/02* (2006.01)

(52) U.S. Cl. .............. 250/522.1; 250/526; 250/493.1; 378/65

(58) Field of Classification Search ............... 250/522.1
See application file for complete search history.

(56) References Cited

U.S. PATENT DOCUMENTS

| | | | |
|---|---|---|---|
| 4,541,293 A * | 9/1985 | Caugant et al. ............. 74/89.18 |
| 6,212,468 B1 * | 4/2001 | Nakayama et al. .......... 701/117 |
| 6,614,871 B1 * | 9/2003 | Kobiki et al. ................. 378/20 |
| 7,132,674 B2 * | 11/2006 | Pastyr et al. ............... 250/505.1 |
| 7,188,999 B2 * | 3/2007 | Mihara et al. ............... 378/197 |
| 7,239,684 B2 * | 7/2007 | Hara et al. .................... 378/65 |
| 7,338,207 B2 * | 3/2008 | Gregerson et al. ........... 378/198 |
| 7,490,982 B2 * | 2/2009 | Gregerson et al. ........... 378/197 |
| 7,672,429 B2 * | 3/2010 | Urano et al. .................. 378/65 |
| 2004/0013239 A1 | 1/2004 | Gregerson et al. |
| 2004/0184579 A1 * | 9/2004 | Mihara et al. ............... 378/65 |
| 2006/0193435 A1 | 8/2006 | Hara et al. |

FOREIGN PATENT DOCUMENTS

| | | |
|---|---|---|
| DE | 103 12 048 A1 | 5/2004 |
| EP | 1 419 801 A1 | 5/2004 |
| EP | 1419801 A1 * | 5/2004 |
| JP | 8-511452 A | 12/1996 |

(Continued)

OTHER PUBLICATIONS

Kamino et al., Int. J. Radiation Oncology Biol. Phys., vol. 66, No. 1, pp. 271-278, 2006.

*Primary Examiner* — Robert Kim
*Assistant Examiner* — Andrew Smyth
(74) *Attorney, Agent, or Firm* — Birch, Stewart, Kolasch & Birch, LLP (57) ABSTRACT

A medical device which can rotate a radiation emitter or the like with high positional precision over an extended period of time is provided. Provided are a support frame installed such that a central axis thereof is positioned substantially horizontally; circular tracks respectively disposed on both side faces of the support frame; a moving gantry configured to revolve relative to the support frame via sliding portions configured to slide on the circular tracks; and revolving driving means for revolving the moving gantry, wherein the moving gantry is constructed of a rigid-framed structure formed of a first side portion and a second side portion disposed so as to flank the support frame from both side faces thereof, and coupling portions for coupling the first side portion and the second side portion.

11 Claims, 5 Drawing Sheets

FOREIGN PATENT DOCUMENTS

| | | |
|---|---|---|
| JP | 10-511595 A | 11/1998 |
| JP | 2000-140134 A | 5/2000 |
| JP | 2001-259058 A | 9/2001 |
| JP | 2003-205042 A | 7/2003 |
| JP | 2004-684 A | 1/2004 |
| JP | 2004-121309 A | 4/2004 |
| JP | 2004-148103 A | 5/2004 |
| JP | 3599995 B2 | 9/2004 |
| JP | 2005-519688 A | 7/2005 |
| JP | 2006-21046 A | 1/2006 |
| JP | 2006-192297 A | 7/2006 |
| JP | 2006192297 A * | 7/2006 |
| JP | 2006-230721 A | 9/2006 |
| WO | WO-94/28971 A2 | 12/1994 |
| WO | WO-97/13552 A1 | 4/1997 |
| WO | WO-03/018132 A1 | 3/2003 |
| WO | WO-2006/076545 A2 | 7/2006 |

* cited by examiner

MEDICAL DEVICE

BACKGROUND OF THE INVENTION

1. Field of the Invention

The present invention relates to medical devices, for example, radiotherapy apparatuses and CT (computed tomography) apparatuses.

2. Description of Related Art

Stereotactic radiotherapy apparatuses are known medical devices for treating affected areas such as tumors by irradiating them with radiation (therapeutic radiation). In such stereotactic radiotherapy apparatuses, the same affected area is irradiated multiple times with radiation from multiple directions. In order to irradiate radiation from multiple directions, it is necessary to provide a radiation emitter which can be moved to and aligned at multiple positions around the patient and which is disposed at a position corresponding to the point where radiation for irradiating the affected area is to be emitted. Known approaches for moving the radiation emitter in this way include the cantilever type, robotic arm type, and gantry type approaches.

In the cantilever type approach, the radiation emitter is supported in a cantilevered manner and rotated around the patient's body. In the robotic arm type approach, the radiation emitter is attached to the end of a multi-axis arm, and the radiation (therapeutic radiation) is radiated from an arbitrary direction. However, with the cantilever type approach or the robotic arm type approach, because of the structure wherein the radiation emitter is attached to the end of the cantilever beam or the arm, the cantilever beam or the arm becomes deformed due to the weight of the radiation emitter, thus making high-precision positioning (irradiation direction setting) difficult.

In contrast, in the gantry type approach, a gantry is positioned so as to surround a patient lying on a couch, and the radiation emitter is moved along the gantry or together with the gantry. The gantry type approach is preferable for realizing high-precision positioning because the radiation emitter is supported by a highly rigid gate-shaped gantry. Medical devices using this gantry type approach have been disclosed, for example, in Japanese Translation of PCT International Application, Publication No. HEI-8-511452 and PCT International Publication No. WO2003/018132 Pamphlet.

With the cantilever type approach and the gantry type approach, in order to increase the degree of freedom of the irradiation direction, positioning control of the couch on which the patient is set (translation and rotation) is performed, in addition to translation of the radiation emitter in a single direction.

Japanese Translation of PCT International Application, Publication No. HEI-8-511452 discloses a radiotherapy apparatus in which a ring-shaped gantry is accommodated inside a radiation barrier, also serving as a housing, and a radiation emitter is provided on the gantry, as shown in FIG. 2 of that publication. In this radiotherapy apparatus, the radiation emitter is rotated by rotating the gantry inside the radiation barrier.

PCT International Publication No. WO2003/018132 Pamphlet discloses a radiotherapy apparatus including a ring-shaped guide, a ring-shaped movable member attached at the inner side of the guide, and a radiation emitter provided on the movable member, as shown in FIGS. 13 to 16 of that publication. In this radiotherapy apparatus, the radiation emitter is rotated by rotating the movable member along the guide.

SUMMARY OF THE INVENTION

However, in the radiotherapy apparatus described in Japanese Translation of PCT International Application, Publication No. HEI-8-511452, a bearing is provided at the outer circumference of the gantry. The gantry itself, as well as components mounted on the gantry, such as a radiation emitter, a detector, and so forth, tends to be pulled down due to gravity. Therefore, with such a bearing structure, support is mainly accomplished by the bearing portion located at the lower side. As a result, it is difficult to ensure positional stability of the gantry. This problem becomes more prominent when there is nonuniform load balance in the gantry according to the rotation angle of the gantry. In addition, partial abrasion centered on the lower part of the bearing shortens the lifespan of the bearing and causes changes in the positioning accuracy of the radiation emitter over time.

Although the radiotherapy apparatus described in PCT International Publication No. WO2003/018132 Pamphlet discloses that the circular rotating member rotates along the guide, it does not disclose any concrete structure for rotating the rotating member with good precision.

With the conventional medical devices as described above, it is difficult to position the gantry and the radiation emitter at an arbitrary angle with good precision.

Japanese Translation of PCT International Application, Publication No. HEI-8-511452 and PCT International Publication No. WO2003/018132 Pamphlet are directed to radiotherapy apparatuses. However, similar problems also occur with medical devices in which a gantry surrounding the patient is rotated about the patient, because of the weight of the gantry. Examples include devices using X-ray tubes instead of radiation emitters, like CT scanners, and devices in which only detectors are installed on the gantry but radiation emitters are not provided, such as PET (positron emission tomography) scanners. In other words, in these conventionally proposed medical devices, it is difficult to ensure a stable and precise positional relationship between the gantry itself, the equipment mounted on the gantry, and the patient over time.

The present invention has been conceived in light of the circumstances described above, and an object thereof is to provide a medical device which can rotate a radiation emitter or the like with high positional precision over an extended period of time.

In order to overcome the problems described above, the medical device of the present invention employs the following solutions.

A medical device according to the present invention comprises a support frame installed such that a central axis thereof is positioned substantially horizontally; circular tracks respectively disposed on both side faces of the support frame; a moving gantry configured to revolve relative to the support frame via sliding portions configured to slide on the circular tracks; and revolving means for revolving the moving gantry. The moving gantry is constructed of a rigid-framed structure (Rahmen structure) formed of a first side portion and a second side portion disposed so as to flank the support frame from both side faces thereof, and coupling portions for coupling the first side portion and the second side portion.

The moving gantry is supported relative to the support frame via the sliding portions, which are formed so as to engage with the circular tracks provided at both sides of the support frame. Because the moving gantry slides on the circular tracks, the support of the moving gantry is accomplished around the entire circumference of the circular tracks. Therefore, it is possible to maintain more stable positioning accuracy of the moving gantry over time, compared to a case where support is accomplished using a bearing which provides support at only one point.

By employing a structure which flanks the support frame and which includes the first side portion and the second side portion, which are held relative to the fixed support frame, and the coupling portions for coupling the first side portion and the second side portion, it is possible to attach the moving gantry to the support frame in such a manner as to allow it to revolve with high rigidity. Accordingly, when the moving gantry revolves, even if there is asymmetry in the load of the equipment mounted on the gantry, such as detectors, with respect to the circumferential direction of the support frame, it is possible to maintain stable positioning accuracy of the moving gantry over time, for the reasons described above.

Furthermore, if the coupling portions are removable, the first side portion and the second side portion can easily be removed from the support frame, thus allowing easy maintenance or replacement of the circular tracks and sliding portions.

The term "revolve" as used here, when applied to the moving gantry, means rotational motion in any direction about an axis extending horizontally, and includes either continuous rotation or rotation by an arbitrary angle.

Because the rigid-framed structure is employed in the moving gantry, it is possible to ensure structural strength while reducing the weight.

In the medical device of the present invention, the sliding portions may be disposed at joints formed in an outer circumferential portion of the rigid-framed structure.

Because the sliding portions are provided at joints formed on the outer circumferential portion of the rigid-framed structure, it is possible to support the load of the moving gantry, as well as the equipment mounted thereon, such as a detector, in an appropriately distributed manner. Therefore, it is possible to ensure more stable positional accuracy of the moving gantry compared to a case in which it is supported partially or locally.

In the medical device of the present invention, the revolving means for the moving gantry is provided on the support frame to which is fixed a revolving driving device for revolving a pinion meshing with a gear provided on at least one of the first side portion or the second side portion.

Because the support frame and the moving gantry have a fixed positional relationship with respect to each other, the gear and the pinion can be made to mesh more stably by securing the revolving driving device to the support frame.

In the medical device of the present invention, a turning driving device for turning the support frame about a substantially vertical axis may be provided at a lower portion of the support frame.

With this turning driving device, it is possible to dispose the detectors or the like provided on the moving gantry with a greater degree of freedom relative to the patient. In other words, by turning the support frame, as well as by revolving the moving gantry about an axis that extends horizontally, for example, the axis of the patient's body, it is possible to rotate the moving gantry also within a plane intersecting a plane orthogonal to the axis of the patient's body, for example. Thus, because the support frame is made to turn, it is not necessary to turn the couch on which the patient is set. Therefore, compared to a case in which the couch on which the patient lies is turned to increase the degree of freedom of the irradiation direction, as in the related art, it is possible to avoid the patient experiencing a sense of unease due to the swinging motion and to avoid changes in the position or state of the target.

The term "turn" as used here, when applied to the support frame, means rotational motion in any direction about an axis extending vertically, and includes continuous rotation or rotation by an arbitrary angle.

In the medical device of the present invention, the support frame may be supported at one point by the turning driving device.

Examples of methods where it is supported at multiple points include a method in which it is installed in the ceiling and the floor via bearings and a method in which it is supported at multiple points by support portions which can slide relative to the floor. In these cases, it is difficult to ensure stable positional accuracy under any turning conditions due to the effects of the positional accuracy of each support portion and the construction accuracy for securing each support portion (for example, the flatness of the floor). In contrast, by providing support at one point, as in the present invention, it is possible to maintain the positional relationship between the isocenter and the equipment mounted on the moving gantry with high precision during turning, independent of the turning angle.

In the medical device of the present invention, a radiation emitter for emitting a beam for irradiation a patient may be provided on the moving gantry.

Examples of the combination of the radiation emitter and the beam emitted from the radiation emitter include a therapeutic-radiation irradiating device and either X-ray or an electron beam, an X-ray tube and X-ray, a laser device and a laser beam, and so forth.

Because the moving gantry is revolved and turned, it is possible to irradiate the patient with a beam from any position. Therefore, it is possible to realize, for example, a stereotactic radiotherapy apparatus.

In the medical device of the present invention, the radiation emitter for emitting the beam for irradiating the patient may be provided on the moving gantry with a swinging mechanism therebetween.

In view of the configuration wherein the radiation emitter revolves together with the moving gantry, it is possible to achieve a swinging motion (pan and/or tilt) of the radiation emitter using the swinging mechanism. Therefore, it is possible to more finely adjust the irradiation region relative to the target on the patient. In addition, since it is not necessary to adjust the couch for this adjustment, it is possible to avoid the patient setting on the couch experiencing a feeling of unease, and in addition, it is possible to shorten the time required for the operator to perform positioning. Furthermore, when irradiating a target that moves over time, such as a lung, it is possible to merely swinging only the radiation emitter, without revolving or turning the moving gantry and the support frame. Therefore, it is possible to carry out high-precision irradiation restricted to the target location by making the irradiation position track the changes in position of the target with good responsiveness.

In the medical device of the present invention, the turning driving device may be installed on a first floor, and a second floor disposed at a height position partially including the lower portion of the support frame, more specifically, lower than the isocenter, is provided on the support frame a predetermined distance above the first floor.

By providing the second floor in this way, it is possible to separate the floor on which the patient, the operator, etc. walk from the floor on which the turning driving device is provided. Therefore, it is possible to prevent the patient, the operator, etc. from making contact with or falling over the turning driving device. By disposing the revolving driving device between the first floor and the second floor, it is possible to avoid accidents such as the patient, the operator, etc. getting stuck between the gear and the pinion, which is a further advantage.

With the medical device according to the present invention, it is possible to set, with good precision, the relative position of the moving gantry, as well as the equipment mounted on the moving gantry, with respect to the isocenter, for any revolutional or turning angle.

With the medical device according to the present invention, it is possible to irradiate the target of the patient, with high precision, with a beam from any revolutional or turning angle.

With the medical device according to the present invention, it is possible to ensure the safety of the patient, the operator, etc. during the revolving operation and the turning operation of the moving gantry and the support frame, respectively.

DETAILED DESCRIPTION OF THE INVENTION

Embodiments of the present invention will be described below with reference to the drawings.

First, the general concept of the radiotherapy apparatus according to this embodiment will be described, and then a detailed description of the present invention will be given.

Figure 1:
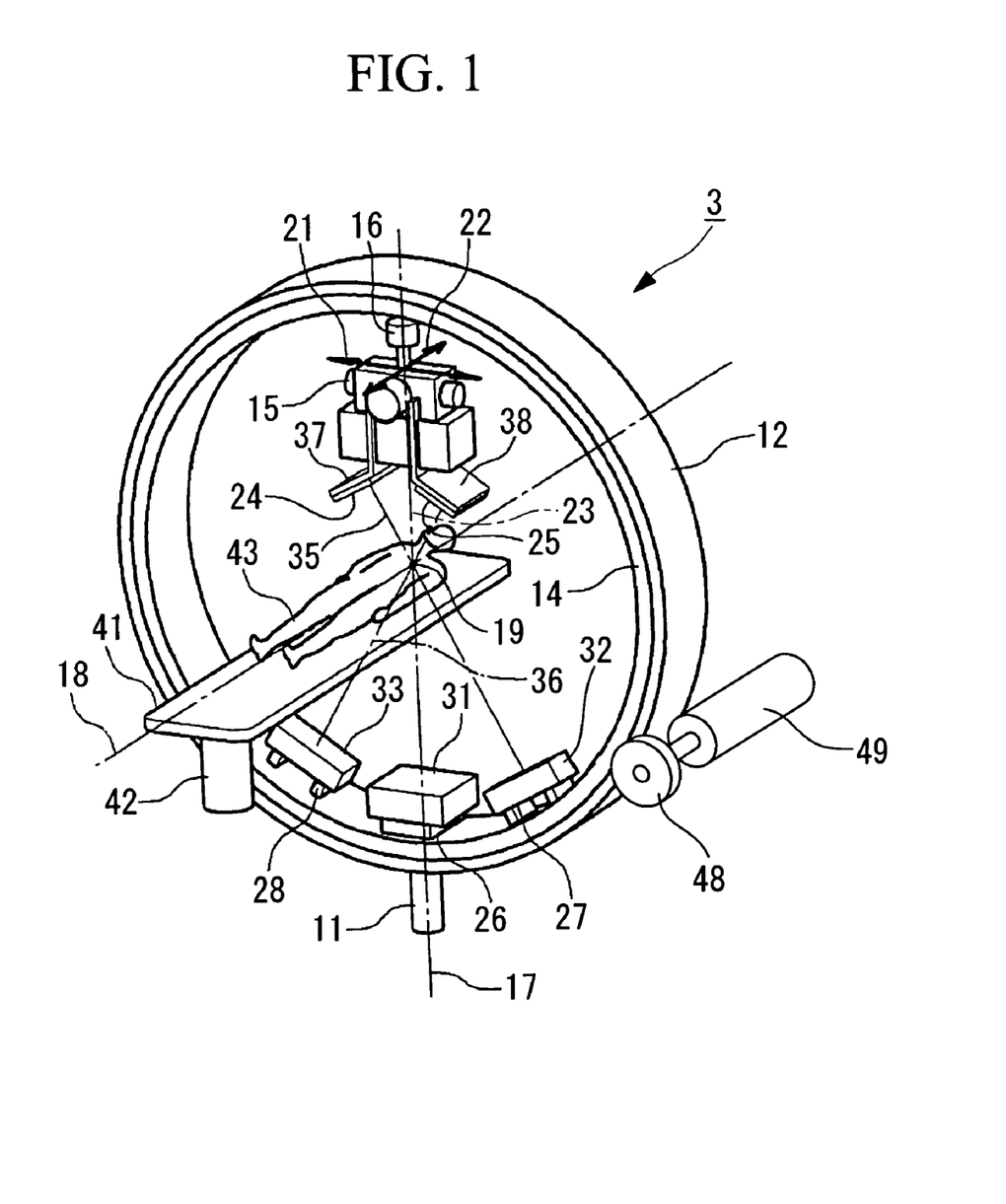
FIG. 1 is a schematic perspective view conceptually illustrating a radiotherapy apparatus according to an embodiment of the present invention.

FIG. 1 shows a schematic perspective view of a radiotherapy apparatus 3 according to this embodiment. The radiotherapy apparatus (medical device) 3 includes a turning driving device 11, a support frame 12, a moving gantry 14, a swinging mechanism 15, and a therapeutic-radiation irradiating device (radiation emitter) 16. Details of the moving gantry 14 will be given later; its configuration is schematically illustrated in FIG. 1.

The turning driving device 11 supports the support frame 12 on a base so as to be capable of turning about a turning axis 17 extending substantially vertically. That is, the support frame 12 is supported at one point by only the turning driving device 11 located therebelow. Rotational control of the turning driving device 11 is performed by a radiotherapy-apparatus control unit (not shown in the drawing).

The support frame 12 is substantially ring-shaped, having an opening at the center. The shape of the support frame 12 in this invention is not limited to ring-shaped. It may be a rectangular shape with an opening at the center thereof. The shape of the support frame 12 is preferably determined from the viewpoint of stability (as the center of gravity becomes lower, the stability increases), structural soundness (deformability), space required for turning, and so forth.

The support frame 12 is installed such that a central axis 18 thereof is positioned substantially horizontally. The moving gantry 14 is supported by the support frame 12 in such a manner as to be capable of revolving along to the support frame 12. The moving gantry 14 revolves about the central axis 18 of the support frame 12. The intersection of the central axis 18, serving as the center of revolution of the moving gantry 14, and the turning axis 17 of the support frame 12 corresponds to an isocenter 19. Revolving control of the moving gantry 14 is performed by the radiotherapy-apparatus control unit (not shown in the drawings).

The swinging mechanism 15 is fixed to the inner circumference side of the moving gantry 14 and supports the therapeutic-radiation irradiating device 16 in such a manner as to be capable of revolving. The swinging mechanism 15 has a pan axis 21 and a tilt axis 22. The pan axis 21 is fixed with respect to the moving gantry 14 and is orthogonal to the central axis 18 of the support frame 12. The tilt axis 22 is fixed with respect to the moving gantry 14 and is orthogonal to the pan axis 21. The swinging mechanism 15 is controlled by the radiotherapy-apparatus control unit (not shown in the drawings) to revolve the therapeutic-radiation irradiating device 16 about the pan axis 21 and to revolve the therapeutic-radiation irradiating device 16 about the tilt axis 22. Thus, the therapeutic-radiation irradiating device 16 radiates therapeutic radiation 23 with a controlled radiation angle.

Because the therapeutic-radiation irradiating device 16 is supported on the moving gantry 14 which revolves with respect to the support frame 12, once the therapeutic-radiation irradiating device 16 is temporarily adjusted so that it points towards the isocenter 19, even if the support frame 12 turns or the moving gantry 14 revolves, the therapeutic radiation 23 always passes substantially through the isocenter 19. Since this can be achieved only when the accuracy is compensated for during revolving of the moving gantry 14, the accuracy during revolving of the moving gantry is important. This point will be discussed later.

The radiotherapy apparatus 3 also includes a plurality of imager systems. More specifically, the radiotherapy apparatus 3 includes radiation-source driving devices 37 and 38, diagnostic X-ray sources 24 and 25, sensor-array driving devices 27 and 28, and sensor arrays 32 and 33.

The radiation-source driving device 37 is fixed to the inner circumference side of the moving gantry 14 and supports the diagnostic X-ray source 24 relative to the moving gantry 14. The radiation-source driving device 37 is controlled by the radiotherapy-apparatus control unit (not shown in the drawing) to move the diagnostic X-ray source 24 relative to the moving gantry 14. The diagnostic X-ray source 24 is disposed at the inner circumference side of the moving gantry 14 and is disposed at a position such that an angle formed by the line joining the isocenter 19 and the diagnostic X-ray source 24 and a line joining the isocenter 19 and the therapeutic-radiation irradiating device 16 is an acute angle. The diagnostic X-ray source 24 is controlled by the radiotherapy-apparatus control unit (not shown in the drawing) to radiate diagnostic X-ray 35 towards the isocenter 19. The diagnostic X-ray 35 is radiated from one point of the diagnostic X-ray source 24 and forms a circular cone-shaped beam with the one point at the apex.

The radiation-source driving device 38 is fixed to the inner circumference side of the moving gantry 14 and supports the diagnostic X-ray source 25 relative to the moving gantry 14. The radiation-source driving device 38 is controlled by the radiotherapy-apparatus control unit (not shown in the drawing) to move the diagnostic X-ray source 25 relative to the moving gantry 14. The diagnostic X-ray source 25 is disposed at the inner circumference side of the moving gantry 14 and is disposed at a position such that an angle formed by a line joining the isocenter 19 and the diagnostic X-ray source 25 and a line joining the isocenter 19 and the therapeutic-radiation irradiating device 16 is an acute angle. The diagnostic X-ray source 25 is controlled by the radiotherapy-apparatus control unit (not shown in the drawing) to radiate diagnostic X-ray 36 towards the isocenter 19. The diagnostic X-ray 36 are radiated from one point on the diagnostic X-ray source 25 and form a circular cone-shaped beam having the one point at the apex thereof.

The sensor-array driving device 27 is fixed to the inner circumference side of the moving gantry 14 and supports the sensor array 32 with respect to the moving gantry 14. The sensor-array driving device 27 is controlled by the radiotherapy-apparatus control unit (not shown in the drawing) to move the sensor array 32 relative to the moving gantry 14.

The sensor-array driving device 28 is fixed to the inner circumference side of the moving gantry 14 and supports the sensor array 33 relative to the moving gantry 14. The sensor-array driving device 28 is controlled by the radiotherapy-apparatus control unit (not shown in the drawing) to move the sensor array 33 relative to the moving gantry 14.

The sensor array 32 receives the diagnostic X-ray 35 radiated by the diagnostic X-ray source 24 and passing through a subject around the isocenter 19, and generates a transmission image of the subject.

The sensor array 33 receives the diagnostic X-ray 36 radiated by the diagnostic X-ray source 25 and passing through the subject around the isocenter 19, and generates a transmission image of the subject.

The sensor arrays 32 and 33 may be, for example, FPDs (flat panel detectors) or X-ray IIs (image intensifiers).

With this imager system, even if the diagnostic X-ray sources 24 and 25 are moved by the radiation-source driving devices 37 and 38, respectively, the sensor arrays 32 and 33 can suitably moved by the sensor-array driving devices 27 and 28 and can generate transmission images centered on the isocenter 19.

The radiotherapy apparatus 3 also includes a sensor-array driving device 26 and a sensor array 31. The sensor-array driving device 26 is fixed to the inner circumference side of the moving gantry 14 and supports the sensor array 31 relative to the moving gantry 14. The sensor-array driving device 26 is controlled by the radiotherapy-apparatus control unit (not shown in the drawing) to move the sensor array 31 relative to the moving gantry 14. The sensor array 31 receives the therapeutic radiation 23 radiated by the therapeutic-radiation irradiating device 16 and passing through the subject around the isocenter 19, and generates a transmission image of the subject. The sensor array 31 may be, for example, an FPD (flat panel detector) or an X-ray II (image intensifier). Even if the therapeutic-radiation irradiating device 16 is moved by the swinging mechanism 15, the sensor array 31 can be suitably moved by the sensor-array driving device 26 and can generate a transmission image centered on the isocenter 19.

The diagnostic X-ray source 24 can also be disposed at a position such that the angle formed by the line joining the isocenter 19 and the diagnostic X-ray source 24 and a line joining the isocenter 19 and the therapeutic-radiation irradiating device 16 is an obtuse angle. In other words, the sensor array 32 is disposed at a position such that the angle formed by the line joining the isocenter 19 and the sensor array 32 and the line joining the isocenter 19 and the therapeutic-radiation irradiating device 16 is an acute angle.

Similarly, the diagnostic X-ray source 25 can also be disposed at a position such that the angle formed by the line joining the isocenter 19 and the diagnostic X-ray source 25 and the line joining the isocenter 19 and the therapeutic-radiation irradiating device 16 is an obtuse angle. In other words, the sensor array 33 is disposed at a position such that the angle formed by the line joining the isocenter 19 and the sensor array 33 and the line joining the isocenter 19 and the therapeutic-radiation irradiating device 16 is an acute angle.

Disposing them in this way is preferable from the viewpoint of protecting the devices, because it is difficult for the sensor array 32 and 33 to be irradiated with the therapeutic radiation 23 radiated from the therapeutic-radiation irradiating device 16.

It is also possible for the radiation-source driving device 37 and 38 to respectively support the diagnostic X-ray sources 24 and 25 relative to the therapeutic-radiation irradiating device 16. Even if the therapeutic-radiation irradiating device 16 is moved by the swinging mechanism 15 at this time, the radiotherapy apparatus 3 affords an advantage in that the relative position with respect to the therapeutic-radiation irradiating device 16 is fixed, and the positions of the diagnostic X-ray sources 24 and 25 are more easily controlled.

A couch 41 is used for setting the patient 43 being treated. The couch 41 includes a restrainer (not shown). This restrainer restrains the patient 43 on the couch 41 so that the patient 43 does not move. A couch-driving device 42 supports the couch 41 on a base and is controlled by the radiotherapy-apparatus control unit (not shown in the drawing) to move the couch 41 so that it is guided inside the opening in the support frame 12.

Figure 2:
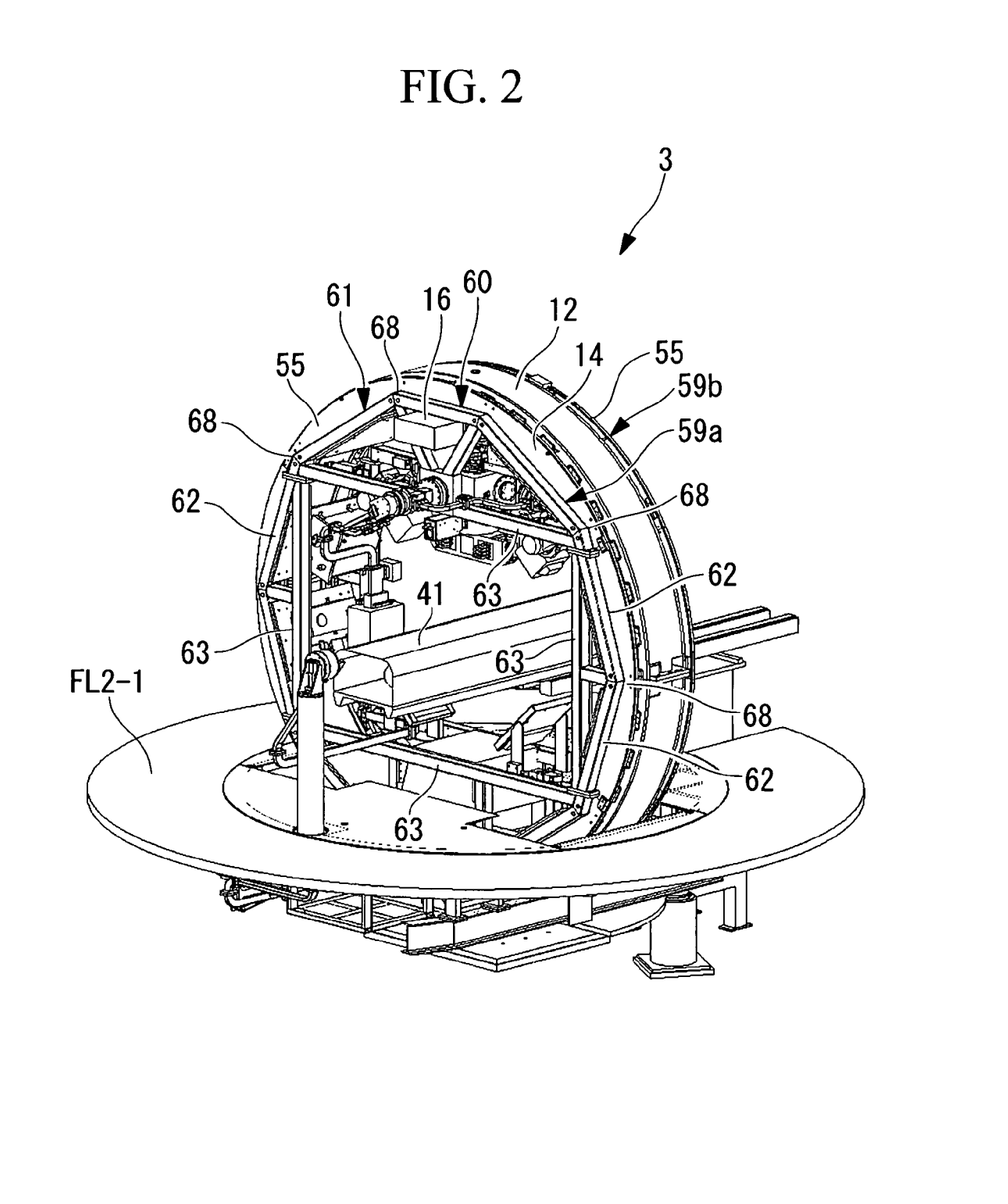
FIG. 2 is a detailed perspective view of the radiotherapy apparatus according to an embodiment of the present invention.

FIG. 2 is a detailed perspective view of the radiotherapy apparatus according to this embodiment. As shown in this figure, the moving gantry 14 is disposed along the support frame 12.

Figure 3:
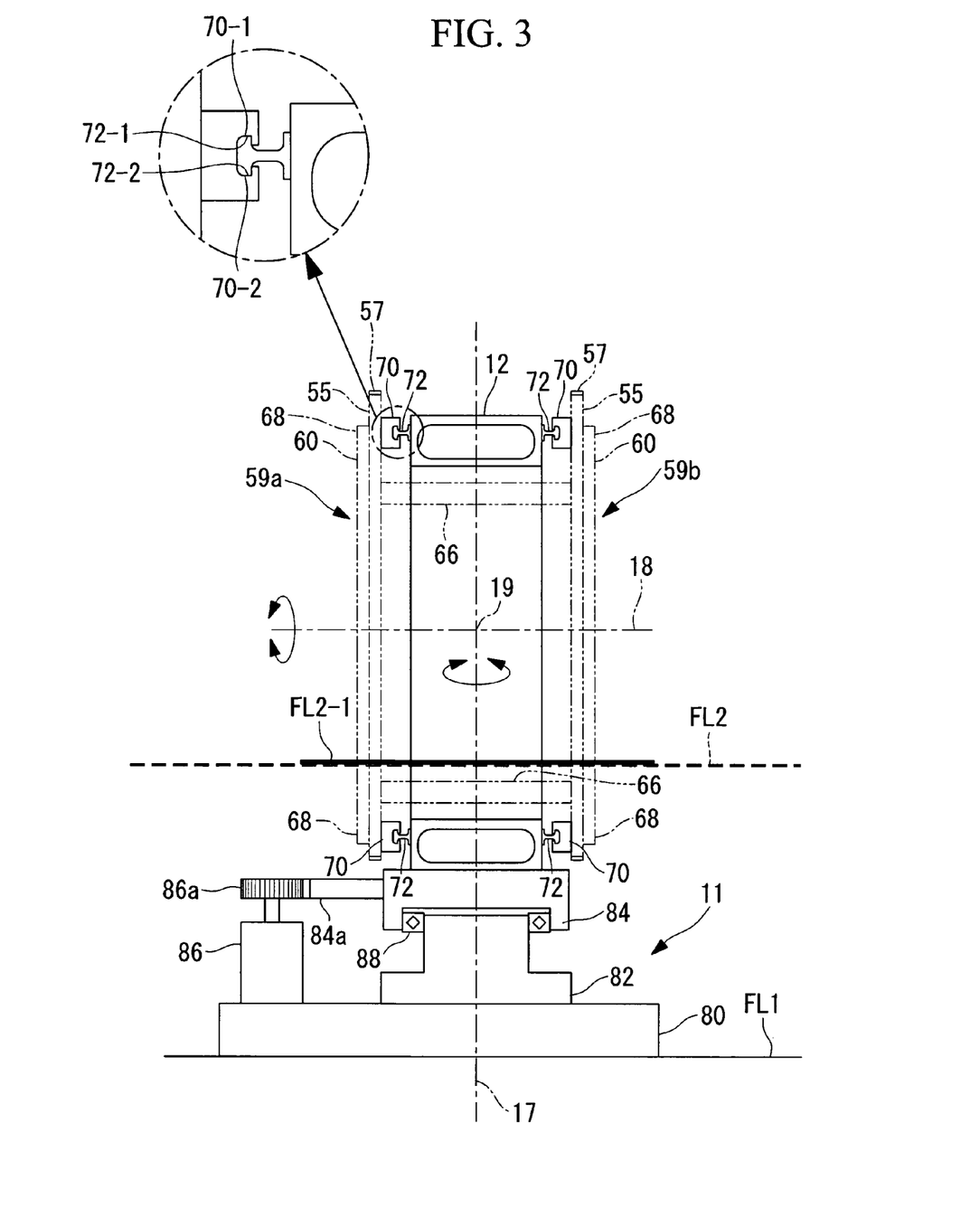
FIG. 3 is a longitudinal sectional view showing principal components of the radiotherapy apparatus in FIG. 2.

FIG. 3 is a longitudinal sectional view of the principal components of the radiotherapy apparatus according to this embodiment.

Figure 5:
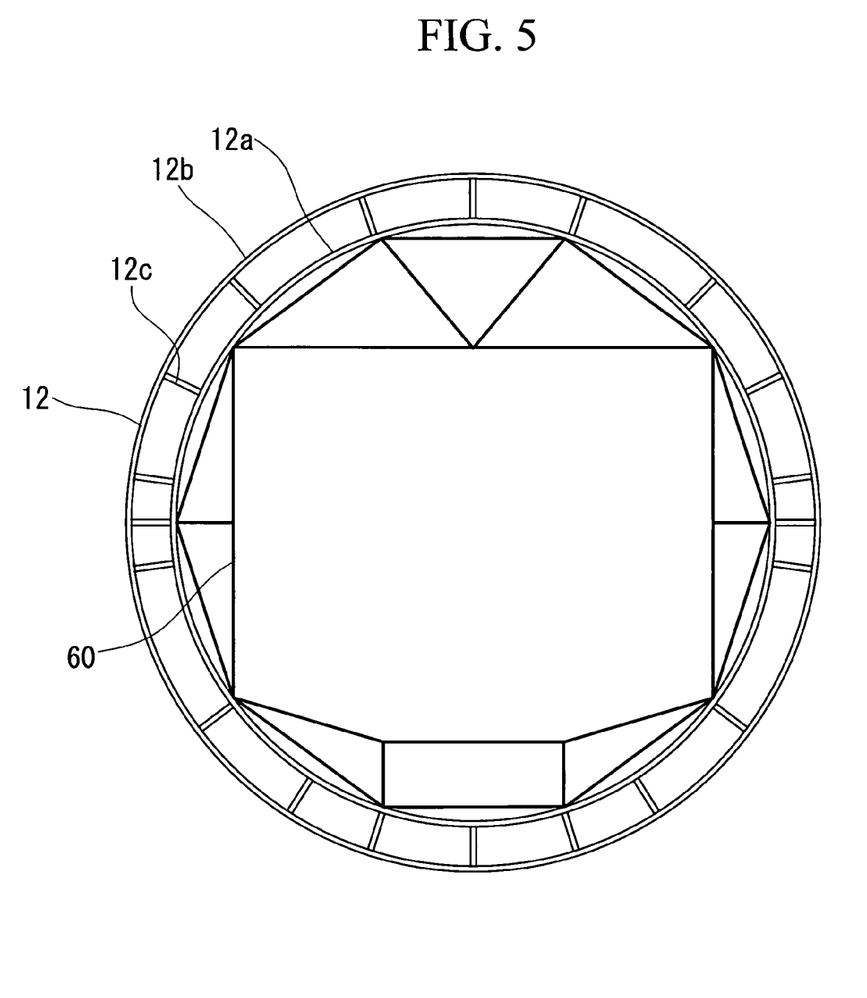
FIG. 5 is a schematic diagram showing the structure of a support frame in the present invention.

As described above, the support frame 12 is substantially ring-shaped having an opening at the center thereof and is installed so that the central axis 18 thereof is disposed substantially horizontally. From the viewpoint of maintaining strength and reducing the weight, as shown in FIG. 3, the cross-section of the support frame 12 is hollow, and as shown in FIG. 5, it is preferable to form it in the shape of a ring forming a structure in which support between a surface 12a facing the isocenter 19 and an opposing surface thereof (the surface at the outer circumferential side) 12b is realized using stabilizing members 12c in the hollow portion. The support frame 12 may be a single, completely integral structure or a plurality of separate structures.

The moving gantry 14 includes a first side portion 59a and a second side portion 59b, which are disposed opposing the two sides of the support frame 12, respectively, as well as coupling beams (coupling portions) 66 for joining the first side portion 59a and the second side portion 59b. The first side portion 59a and the second side portion 59b are each formed of a side rigid-framed structure 60 and a ring-shaped plate 55.

As shown in FIG. 3, the first side portion 59a and the second side portion 59b are rigidly connected by the plurality of coupling portions 66 disposed at the inner circumferential side of the support frame 12. These coupling portions 66 can be attached and removed, for example using bolts, so as to facilitate regular maintenance and replacement of the components of the first side portion 59a, the second side portion 59b, and the support frame 12. The coupling portions 66 extend in the direction along the central axis 18 of the support frame 12 and are disposed at predetermined intervals in the circumferential direction of the support frame 12. In this way, the moving gantry 14 is sandwiched from the inner circumferential side of the support frame 12 by the first side portion 59a and the second side portion 59b located at both sides and by the coupling portions 66.

At both side faces of the support frame 12, circular-tracks 72, formed as circular rails, are fixed coaxially with the central axis 18. The first side portion 59a and the second side portion 59b of the moving gantry 14 are engaged with the support frame 12 via the circular-tracks 72. In addition, the first side portion 59a and the second side portion 59b have substantially the same shape. In other words, the first side portion 59a and the second side portion 59b of the moving gantry 14 are disposed substantially symmetrically with respect to the support frame 12. The first side portion 59a and the second side portion 59b each include the ring-shaped plate 55 disposed facing the side faces of the support frame 12. That is, the ring-shaped plates 55 are disposed at both sides of the support frame 12. As shown in FIG. 3, gears 57 for revolving the moving gantry 14 are provided at the outer peripheral edges of the ring-shaped plates 55. A pinion 48 that is rotationally driven by a revolving driving device 49 is meshed with the gears 57 on the ring-shaped plates 55, thereby revolving the moving gantry 14. As shown in this embodiment, the configuration wherein the gears 57 and the pinions 48 are meshed at both the first side portion 59a and the second side portion 59b allows similar driving forces to be applied to both sides, which is preferable in view of enabling smoother sliding. However, a structure in which the gear and the pinion are meshed with the ring-shaped plate at only one side also allows the gantry 14 to revolve.

Figure 4:
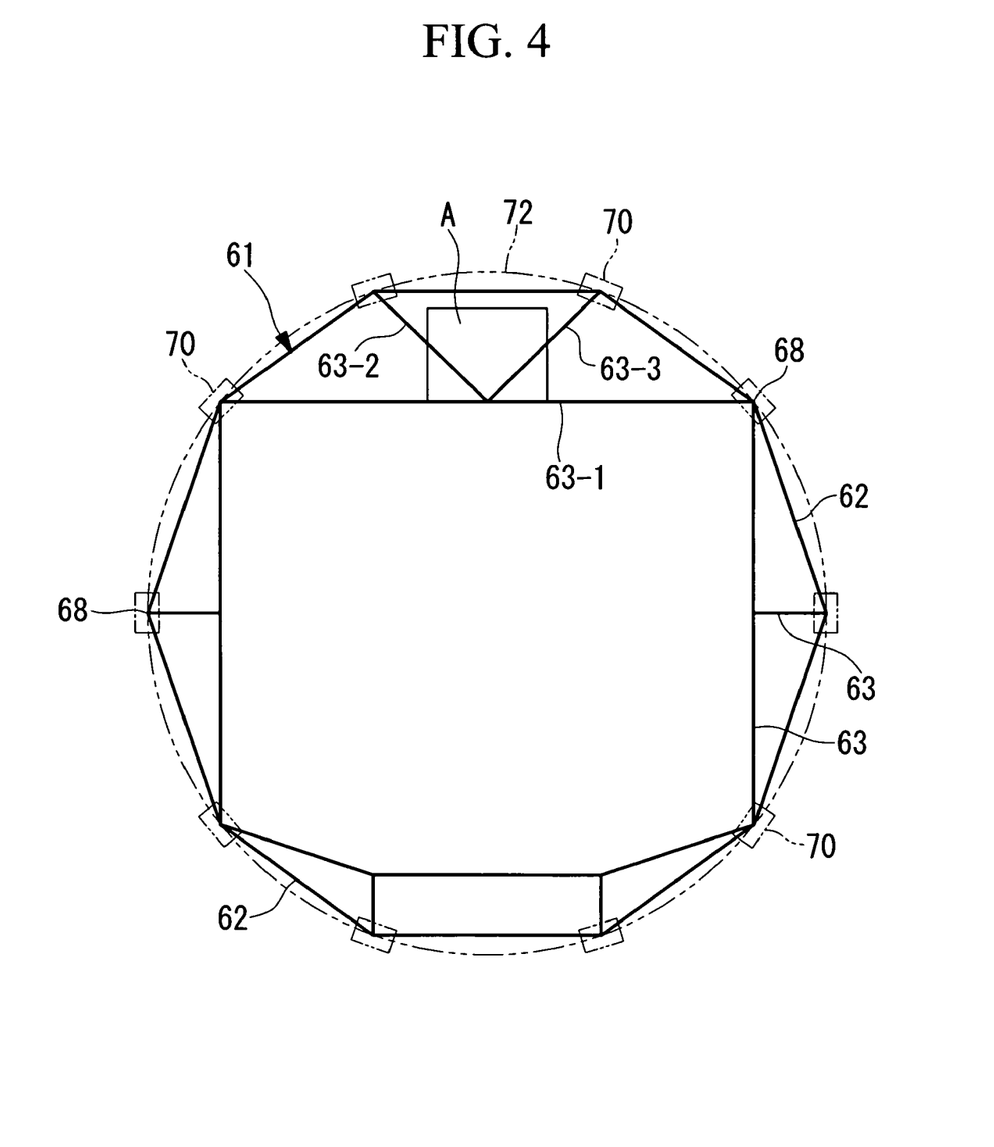
FIG. 4 is a diagram illustrating the positional relationship between a side rigid-framed structure and a sliding portion.

The side rigid-framed structure 60 have sufficient strength to ensure structural integrity for the loads of the moving gantry 14 itself, as well as the therapeutic-radiation irradiating device 16 and so forth supported by the moving gantry 14, and also holds the ring-shaped plates 55. Each side rigid-framed structure 60 includes a polygonal frame 61 formed by joining a plurality of braces 62 around the circumferential direction of the ring-shaped plates 55, that is, around the circumferential direction of the support frame 12. FIG. 4 shows an example in which the polygonal frame 61 is a decagon.

The joints of the braces 62 of the side rigid-framed structure 60 are rigidly formed by welding or bolting. Internal frames 63 are fixed so as to have common joints 68 with the polygonal frame 61, so as to reinforce the polygonal frame 61 from the inside. The positions of the internal frame 63 are set at this time on the basis of the support locations and weights of the components supported by the moving gantry 14 so that the loads on the joints 68 do not become unbalanced. For example, as shown in FIG. 4, when the therapeutic-radiation irradiating device 16 is disposed between the first side portion 59a and the second side portion 59b, corresponding to position A, it is necessary to set the position of internal frame 63-1 so that the relative positional relationship of the therapeutic-radiation irradiation device 16 and the isocenter 19 is appropriate, and to dispose internal frames 63-2 and 63-3 so that the weight of the therapeutic-radiation irradiating device 16 can be supported in a distributed manner. Thus, the position of each internal frame 63 is determined considering the weight, position, and size of the components supported on the moving gantry 14.

As shown in FIG. 4, sliding portions 70 are fixed at positions corresponding to each joint 68 (see FIG. 2) which correspond to the corner portion of the polygonal frame 61 of the side rigid-framed structure 60. FIG. 4 shows an example in which the sliding portions 70 are provided at all joints 68 at substantially equal intervals; however, they may be disposed intermittently according to the load distribution. Moreover, the sliding portions 70 may be disposed at the braces 62 to distribute the load, so long as the strength of the braces 62 is ensured. The sliding portions 70 travel along the circular-tracks 72 provided at both sides of the support frame 12.

As shown in FIG. 3, as the sliding portion 70, it is preferable to use a structure which slides while surrounding the ridge of the circular-tracks 72 so as to enclose it. One possible example of the sliding portions 70 is LM blocks (registered trademark). With this structure, the sliding portions 70 at all of the joints 68 contact at least one surface of the circular-tracks 72. That is to say, although the entire moving gantry 14 tends to fall vertically downward, at that time, at the uppermost portion, a sliding-portion groove surface 70-1 always engages with a circular-track side face 72-1, and at the lowermost portion, a sliding-portion groove surface 70-2 always engages with a circular-track side face 72-2. In addition, at other arbitrary positions, except at points where the sliding portions 70 are vertical, either face always engages, according to the position of the sliding portion 70. Hence, the moving gantry 14 is supported at multiple points, and it is therefore possible to maintain stable positioning accuracy over time.

FIG. 3 shows the turning driving device 11 which turns the support frame 12 about the turning axis 17. The turning driving device 11 includes a turning shaft 82 disposed on a base 80 which is secured to a first floor FL1, a turning block 84 disposed above the turning shaft 82 so as to be turnable via a bearing 88, and a turning motor 86 which applies a turning driving force.

The turning block 84 and the support frame 12 are fixed so that the support frame 12 turns together with the turning block 84. A gear 84a is provided at the side of the turning block 84, and a pinion 86a driven by the turning motor 86 is meshed with this gear 84a. By rotating the pinion 86a with the turning motor 86, the turning block 84 and the support frame 12 are made to turn via the gear 84a. From the viewpoint of maintaining the relative positions of the gear 84a and the pinion 86a, it is preferable to secure the turning motor 86 to the base 80, as shown in FIG. 3.

The radiotherapy apparatus 3 with the above-described configuration is used as follows.

First, the patient 43 lies on the couch 41, and then the couch 41 is moved so as to be guided into the opening of the support frame 12.

Then, the position of the couch 41 is controlled using the diagnostic X-ray 35 and 36 so that the affected area of the patient is located at the isocenter 19. The swinging mechanism 15 is controlled as required so that the therapeutic radiation 23 passes through the affected area.

The moving gantry 14 is aligned after being revolved about the central axis 18 so that the therapeutic-radiation irradiating device 16 is positioned at a radiation angle determined according to a treatment plan. In this state, the therapeutic radiation 23 is radiated from the therapeutic-radiation irradiating device 16 towards the affected area. If the affected area shifts during irradiation, as in the case of a lung, the therapeutic-radiation irradiating device 16 is dynamically driven by the swinging mechanism 15 so that the therapeutic radiation 23 tracks that shifting.

Once a predetermined amount of radiation has been radiated, the therapeutic radiation 23 is stopped, and thereafter, the moving gantry 14 is revolved and aligned so that the therapeutic-radiation irradiating device 16 is located at the next radiation angle determined according to the treatment plan. Then, in the same way as described above, the therapeutic radiation 23 is radiated towards the affected area.

The therapeutic radiation 23 is radiated from a desired angle by operating the turning driving device 11, as required, to turn the support frame 12 about the turning axis 17. By providing this turning function, the degree of freedom of the radiation direction is increased compared to the case where only the revolving function of the moving gantry 14 is provided. It has been proposed that the couch 41 be revolved about a vertical axis as a similar means for increasing the degree of freedom. However, providing the turning function in the main apparatus, as in the present invention, is preferable in that it is possible to eliminate mental stress on the patient 43 as rotating motion is applied to his or her body, as well as variations in the condition and position of the affected area as the couch 41 turns.

According to this embodiment, it is possible to realize the following advantages.

The moving gantry 14 is supported relative to the support frame 12 via the sliding portions 70 which are formed so as to be engaged with the circular-tracks 72 provided at both sides of the support frame 12. Because the moving gantry 14 slides on the circular-tracks 72, the moving gantry 14 is supported around the entire circumference of the circular-tracks 72. Therefore, it is possible to maintain stable positioning accuracy of the moving gantry 14 over time compared to the case using a bearing, which supports it at only one point.

By employing a construction in which the support frame 12 is held between the first side portion 59a, the second side portion 59b, and the coupling beams 66 with respect to the fixed support frame 12, it is possible to attach the moving gantry 14 to the support frame 12 with high rigidity while allowing it to revolve. Accordingly, even in the event of asymmetry in the load of the equipment mounted to the moving gantry 14, such as detectors, relative to the circumferential direction of the support frame 12, which occurs when the moving gantry 14 is revolved, it is possible to maintain stable positioning accuracy of the moving gantry 14 over time, for the reasons described above.

By removing the coupling beams 66, it is possible to easily remove the first side portion 59a and the second side portion 59b from the support frame 12, and therefore, it is possible to simplify maintenance and replacement of the circular-tracks 72 and the sliding portions 70.

Since a rigid-framed structure is employed in the moving gantry 14, it is possible to reduce the weight while ensuring strength.

Furthermore, since the moving gantry 14 is supported by the sliding portions 70 disposed at positions corresponding to the joints 68 of the rigid-framed structure, it is possible to support the load of the moving gantry 14 in a suitably distributed manner. Therefore, it is possible to ensure stability and positional accuracy of the moving gantry 14.

In addition, since the plurality of sliding portions 70 are arranged at predetermined intervals in the circumferential direction and the load is always borne by the plurality of sliding portions 70 regardless of the orientation of the moving gantry 14, it is possible to revolve the moving gantry 14 with good precision.

As means for revolving the moving gantry 14, the revolving driving device 49 is provided on the fixed support frame 12 for revolving the pinion 48, which is engaged with the gear 57 disposed on at least one of the first side portion 59a and the second side portion 59b. Because the support frame 12 and the moving gantry 14 have a fixed positional relationship relative to each other, by securing the revolving driving device 49 to the support frame 12, it is possible to mesh the pinion 48 with the gear more stably.

Arranging the pinion 48 to mesh with the gears 57 of both the first side portion 59a and the second side portion 59b allows the same driving force to be applied to both sides, which is preferable in that it allows smooth sliding.

As described in this embodiment, by revolving using the gears 57 provided on the outermost peripheral portion of the ring-shaped plates 55, it is possible to reduce the required force exerted for this operation, which facilitates fine positional adjustment of the corresponding pinion 48; therefore, it is possible to achieve a more stable revolving operation at lower cost.

Providing the turning driving device 11 below the support frame 12 for turning the support frame 12 about the substantially vertical axis allows the detectors and so forth installed on the moving gantry 14 to be arranged relative to the patient 43 with a greater degree of freedom. In other words, by turning the support frame 12 in addition to revolving the moving gantry 14 in a plane orthogonal to the axis of the body of the patient 43, it is possible to revolve the moving gantry 14 in a plane intersecting the plane orthogonal to the body axis of the patient 43. Because the support frame 12 is turned in this way, it is not necessary to turn the couch 41 on which the patient 43 lies. Therefore, compared to a case in which the couch itself is turned, with the patient lying thereon, to increase the degree of freedom of the radiation direction, as in the related art, it is possible to avoid a sense of unease in the patient due to the swinging motion, as well as changes in the position or condition of the target.

Because the support frame 12 is supported at one point by the turning driving device 11, the precision for installing each support portion and the manufacturing precision for securing each support portion (for example, the flatness of the floor) has no effect, unlike the case where it is supported at multiple points, and it is possible to maintain a highly precise positional relationship between the components installed on the moving gantry 14 and the isocenter 19 during turning, independently of the turning angle.

Because the radiation emitter which emits the beam for irradiating the patient 43 is provided on the moving gantry 14, it is possible to radiate the beam from any position with respect to the patient 43. Thus, it is possible to realize, for example, Stereotactic radiotherapy.

Because the therapeutic-radiation irradiating device 16 is provided on the moving gantry 14 via the swinging mechanism 15, it is also possible to more finely adjust the irradiation region relative to the target on the patient. Furthermore, since it is not necessary to precisely move the couch 41 for this adjustment, it is possible to avoid a feeling of unease in the patient lying on the couch, and it is also possible to reduce the time required for an operator to perform positioning. If the target, such as a lung, moves during irradiation, it is acceptable merely to swinging only the therapeutic-radiation irradiating device 16, without revolving or turning the moving gantry 14 and the support frame 12; therefore, by making the irradiation position track the changes in position of the irradiation site with good responsiveness, it is possible to perform irradiation with high precision.

As shown in FIG. 3, in this embodiment, the turning driving device 11 is installed on the first floor FL1, and a second floor FL2 is provided a predetermined distance above this first floor FL1. Here, the second floor FL2 is positioned lower than the isocenter 19. The second floor FL2 is divided so that it can support the turning operation: a second floor FL2-1 forming one part thereof is connected to the support frame 12 and can revolve relative to the other second floor FL2. FIG. 2 shows this revolvable second floor FL2-1.

The turning driving device 11 and the revolving driving device 49 are disposed between the first floor FL1 and the second floor FL2.

By providing the second floor FL2 in this way, it is possible to separate the floor on which the patient 43, the operator, etc.

walk from the floor FL1 on which the turning driving device 11 is installed. Therefore, it is possible to avoid the patient, operator etc. making contact with or tripping over the turning driving device 11. Also, as well as facilitating access to the radiotherapy apparatus 3 by the patient, the operator, etc., the distance from the isocenter position to the floor on which the patient, the operator, etc. walks (the second floor FL2) is reduced, and therefore, the ease of use for the operator is improved when adjusting the position of the couch 41, while providing a sense of security to the patient on the couch.

To turn the radiotherapy apparatus 3 about the turning axis 17, it is necessary to provide an opening in the second floor FL2; however, by constructing the portion FL2-1 of the second floor FL2 to turn together with the radiotherapy apparatus during the turning operation, it is possible to prevent someone falling down towards the first floor through the opening.

By disposing the revolving driving device 49 between the first floor FL1 and the second floor FL2, it is possible to avoid accidents such as the patient, the operator, etc. getting caught between the gear 57 and the pinion 48 of the revolving driving device 49. In addition, the overall apparatus can be made more compact by effectively using the space between these floors.

The embodiments above have been described in terms of a stereotactic radiotherapy apparatus as one example of a medical device. However, the present invention is not limited thereto. It is also possible to apply it in a similar fashion to other types of medical devices, such as CT (computed tomography) or particle-beam therapy apparatuses, PET (positron emission tomography), laser diagnosis/treatment apparatuses, and so forth.

What is claimed is:

1. A medical device, comprising:
   a support frame installed such that a central axis thereof is positioned substantially horizontally;
   circular-tracks respectively disposed on both side faces of the support frame;
   a moving gantry configured to revolve concentrically with respect to the central axis of the support frame via sliding portions that are arranged at a predetermined interval along an entire circumference of each of the circular-tracks so that the sliding portions slide on the circular tracks; and
   revolving means for revolving the moving gantry,
   wherein the moving gantry is constructed of a rigid-framed structure formed of a first side portion and a second side portion disposed so as to flank the support frame from both side faces thereof, and coupling portions for coupling the first side portion and the second side portion,
   the rigid-frame structure includes a polygonal frame formed by joining a plurality of braces along a circumference of the support frame,
   the coupling portions are located on a radially inner side of the support frame, and
   the sliding portions are disposed at joints formed in an outer circumferential portion of the rigid-framed structure or in a neighborhood of the joints.

2. A medical device according to claim 1, wherein the sliding portions are disposed at joints formed in an outer circumferential portion of the rigid-framed structure.

3. A medical device according to claim 1, wherein the revolving means comprises
   a gear disposed on at least one of the first side portion and the second side portion;
   a pinion configured to mesh with the gear; and
   a revolving driving device disposed on the support frame and configured to revolve the pinion.

4. A medical device according to claim 1, further comprising:
   a turning driving device configured to turn the support frame about a substantially vertical axis provided at a lower portion of the support frame.

5. A medical device according to claim 4, wherein the support frame is supported at one point by the turning driving device.

6. A medical device according to claim 1, wherein a radiation emitter configured to emit a beam for irradiation a patient is provided on the moving gantry.

7. A medical device according to claim 6, wherein the radiation emitter is provided on the moving gantry with a swinging mechanism therebetween.

8. A medical device according to claim 4, wherein
   the turning driving device is installed on a first floor, and
   a second floor disposed at a height position partially including the lower portion of the support frame is provided on the support frame a predetermined distance above the first floor.

9. A medical device according to claim 8, wherein the turning driving device is disposed between the first floor and the second floor.

10. A medical device, comprising:
    a support frame installed such that a central axis thereof is positioned substantially horizontally;
    circular-tracks respectively disposed on both side faces of the support frame;
    a moving gantry configured to revolve relative to the support frame via sliding portions that are arranged at a predetermined interval along an entire circumference of each of the circular-tracks so that the sliding portions slide on the circular tracks; and
    revolving means for revolving the moving gantry,
    wherein the moving gantry is constructed of a rigid-framed structure formed of a first side portion and a second side portion disposed so as to flank the support frame from both side faces thereof, and coupling portions for coupling the first side portion and the second side portion,
    the rigid-frame structure includes a polygonal frame formed by joining a plurality of braces along a circumferential direction of the support frame,
    a turning driving device configured to turn the support frame about a substantially vertical axis is provided at a lower portion of the support frame,
    the turning driving device is installed on a first floor,
    a second floor disposed at a height position partially including the lower portion of the support frame is provided on the support frame a predetermined distance above the first floor, and
    the sliding portions are disposed at joints formed in an outer circumferential portion of the rigid-framed structure or in a neighborhood of the joints.

11. A medical device according to claim 10, wherein the turning driving device is disposed between the first floor and the second floor.

* * * * *